United States Patent [19]

Smith et al.

[11] Patent Number: 5,122,515

[45] Date of Patent: Jun. 16, 1992

[54] NUTRIENT COMPOSITION CONTAINING DIPEPTIDES AND METHOD FOR ADMINISTERING THE SAME

[76] Inventors: Ross C. Smith, 32 Crowther Avenue, Greenwich, NSW 2065; Brian P. Walker, 8 Hammers Rd., Northmead, NSW 2152, both of Australia

[21] Appl. No.: 525,450

[22] Filed: Jun. 19, 1990

[51] Int. Cl.$^5$ ................................. C07K 5/06
[52] U.S. Cl. .................... 514/19; 426/656; 426/657
[58] Field of Search .................. 514/19; 426/656

[56] References Cited

U.S. PATENT DOCUMENTS

| | | | |
|---|---|---|---|
| 4,340,592 | 7/1982 | Adibi | 424/177 |
| 4,636,490 | 1/1987 | Martinez et al. | 514/15 |
| 4,758,675 | 2/1988 | Hansen, Jr. et al. | 549/77 |

FOREIGN PATENT DOCUMENTS

| | | |
|---|---|---|
| 0087750 | 7/1983 | European Pat. Off. |
| 0087751 | 7/1983 | European Pat. Off. |
| 0182356 | 5/1986 | European Pat. Off. |
| 0346501 | 12/1989 | European Pat. Off. |
| 0399656 | 11/1990 | European Pat. Off. |
| 3206810 | 12/1983 | Fed. Rep. of Germany |
| 3206784 | 5/1985 | Fed. Rep. of Germany |

OTHER PUBLICATIONS

Ltd., London, GB & JP-A-2023849, Abstract only, Jan. 26, 1990.
Burns et al., Arginine: An Indispensable Amino Acid for Mature Dogs, J. Nutr. 111: 1020-1024, 1981.
Chyun et al., Improvement of Nitrogen Retention by Arginine and Glycine Supplementation and Its Relation to Collagen Synthesis in Traumatixed Mature and Aged Rats, J. Nutr. 114: 1697-1704, 1984.
Czarnecki et al., Urea Cycle Function in the Dog with Emphasis on the Role of Arginine, J. Nutr. 114: 581-590, 1984.
Fahey et al., Effect of L-Arginine on Elevated Blood Ammonia Levels in Man, American Journal of Medicine, 860-869.
Brusilow, Arginine, an Indispensable Amino Acid for Patients with Inborn Errors of Urea Synthesis, J. Clin. Invest., vol. 74, Dec. 1984, 2144-2148.
Rudman et al., Hypotyrosinemia, Hypocystinemia, and Failure to Retain Nitrogen During Total Parenteral Nutrition of Cirrbotic Patients, Gastroenterology 1981:81:1025-35.
Rose, The Amino Acid Requirements of Adult Man, Nutirtion Abstracts and Reviews, vol. 27, No. 3, Jul. 1957, 631-647.
Laidlaw et al., Newer Concepts of the Indispensable Amino Acids, Am J Clin Nutr 1987; 46:593-605.
du Ruisseau et al., Studies on the Metabolism of Amino Acids and Related Compounds in Vivo. IV. Blood Ammonia and Urea Levels Following Intraperitoneal Administration of Amino Acids and . . . , Archives of Biochemistry and Biophysics 64, 355-367 (1956).
Brown et al., Transiently Reduced Activity of Carbamyl Phosphate Synthetase and Ornithine Transcarbamylase in Liver of Children with Reye's Syndrome, N. Engl J. Med, vol. 294, No. 16, 861-867, 1976.
Barbul et al., Immunostimulatory Effects of Arginine in Normal and Injured Rats, Journal of Surgical Research 29, 228-235 (1980).
Barbul et al., Arginine: Biochemistry, Physiology, and Therapeutic Implications, J. of Parenteral and Enteral Nutrition, vol. 10, No. 2, 1986, 227-238.

(List continued on next page.)

Primary Examiner—Howard E. Schain
Assistant Examiner—Choon P. Koh
Attorney, Agent, or Firm—Hill, Van Santen, Steadman & Simpson

[57] ABSTRACT

This invention relates to a nutrient composition containing a dipeptide and method for administering the same. Particularly, this invention relates to a dipeptide tyrosyl-arginine, comprised of the amino acids tyrosine and arginine and the use of this dipeptide as a nutrient supplement to intravenous nutrition.

8 Claims, 1 Drawing Sheet

OTHER PUBLICATIONS

Anderson et al., Lysine and Arginine Requirements of the Domestic Cat, 1368–1372.

Abel et al., Improved Survival from Acute Renal Failure After Treatment With Intravenous Essential L-Amino Acids and Glucose, The New England Journal of Medicine, vol. 288, No. 14, Apr. 5, 1973, 695–699.

Anderson et al., Effects of Excess Arginine With and Without Supplemental Lysine on Performance, Plasma Amino Acid Concentrations and Nitrogen Balance of Young Swine, Journal of Animal Science, vol. 58, No. 2, 1984, 396–377.

Steininger et al., Infusion of Dipeptides as Nutritional Substrates for Glutamine, Tyrosine, and Branched-Chain Amino Acids in Patients with Acute Pancreatitis, Metabolism, vol. 38, No. 8, 1989, 78–81.

Stehle et al., Effect of Parenteral Glutamine Peptide Supplements on Muscle Glutamine Loss and Nitrogen Balance After Major Surgery, The Lancet, 231–233, 1989.

Hubl et al., Influence of Molecular Structure and Plasma Hydrolysis on the Metabolism of Glutamine-Containing Dipeptides in Humans, Metabolism, vol. 38, No. 8, 1989, 59–62.

Furst et al., Stress-Induced Intracellular Glutamine Depletion, Contr. Infusion Ther. Clin. Nutr., vol. 17 (1987), 117–136.

Brandl et al., Parenteral Nutrition with an Amino Acid Solution Containing a Mixture of Dipeptides, Evidence for Efficient Utilization of Dipeptides in Man, Contr. Infusion Ther. Clin. Nutr. 17, (1987), 103–116.

Albers et al., Availability of Amino Acids Supplied by Constant Intravenous Infusion of Synthetic Dipeptides in Healthy Man, Clinical Science (1989), 76, 643–648.

Albers et al., Availability of Amino Acids Supplied Intravenously in Healthy Man as Synthetic Dipeptides; Kinetic Evaluation of L-Alanyl-L-Glutamine and Glycyl-L-Tyrosine, Clinical Science (1988) 75, 463–468.

Adibi, Experimental Basis for Use of Peptides as Substrates for Parenteral Nutrition: A Review, Metabolism, vol. 36, No. 10 (1987) 1001–1011.

Adibi, Intravenous Use of Glutamine in Peptide Form: Clinical Applications of Old and New Observations, Metabolism, vol. 38, No. 8 (1989), pp. 89–92.

Adibi et al., Influence of Molecular Structure on Half-Life and Hydrolysis of Dipeptides in Plasma: Importance of Glycine as N-Terminal Amino Acid Residue, Metabolism, Col. 35, No. 9 (1986), 830–836.

Gopalakrishna et al., Effect of Growth & Differentiation on Distribution of Arginase & Arginine in Rat Tissues, Indian Journal of Biochemistry & Biophysics, vol. 16, Apr. 1979, 66–68.

De Aloysio et al., The Clinical Use of Arginine Aspartate in Male Infertility, Acta Eut Fertil 1982; 13: 133–67.

Deshmukh et al., Arginine Requirement and Ammonia Toxicity in Ferrets, J. Nutr. 113: 1983, 1664–1667.

Carey et al., An Arginine-Deficient Diet in Humans Does Not Evoke Hyperammonemia or Orotic Aciduria, American Institute of Nutrition (1987) 1734–1739.

Brusilow et al., Arginine Therapy of Argininosuccinase Deficiency, The Lancet, Jan. 29, 1979, 124–127.

Arginine as an Essential Amino Acid in Children With Argininosuccinase Deficiency, Nutrition Reviews, vol. 37, No. 4, 1979, 112–113.

Elsair et al., Effect of Arginine Chlorhydrate on Nitrogen Balance During the Three Days Following Routine Surgery in Man, Biomedicine, 1978, 29, 312–317.

Ueda et al., Kyotorphin (Tyrosine-Arginine) Synthetase in Rat Brain Synaptosomes, The Journal of Biological Chemistry, vol. 262, No. 17, 1987, 8165–8173.

Takagi et al., A Novel Analogesic Dipeptide from Bovine Brain is a Possible Met-Enkephalin Releaser, Nature, vol. 282, 1979, 410–412.

Ueda et al., A Met-Enkephalin Releaser (Kyotorphin)-Induced Release of Plasma Membrane-Bound $Ca^2$ From Rat Brain Synaptosomes, Brain Research 419 (1987) 197–200.

Furst et al., Stress-Induced Intracellular Glutamine Depletion, Contr. Infusion Ther. Clin. Nutr., vol. 27, (1987), 117–136.

Auspen, 16th Annular Scientific Meeting, 18–19, Tyrosine-Arginine (Tyr-Arg): A Soluble Form of Tyrosine.

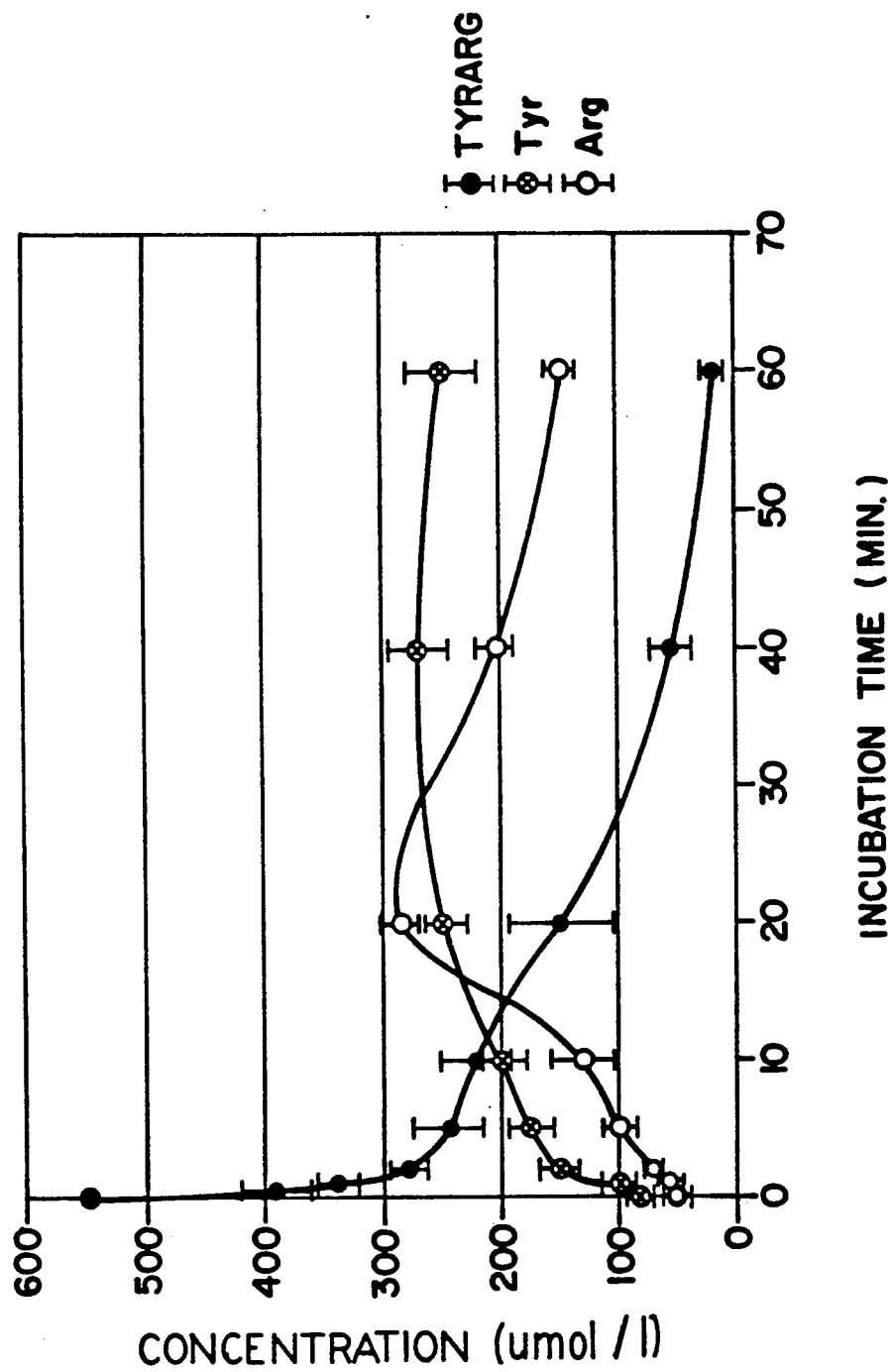

NUTRIENT COMPOSITION CONTAINING DIPEPTIDES AND METHOD FOR ADMINISTERING THE SAME

BACKGROUND OF THE INVENTION (1) Field of the invention

This invention relates to a dipeptide, tyrosyl-arginine, comprised of the amino acids tyrosine and arginine and the use of this dipeptide as a nutrient supplement to intravenous nutrition.

(2) Description of Related Art

Intravenous nutrition has become an important therapy for patients who are unable to adequately nourish themselves by oral nutrition. While current methods of intravenous nutrition allow the maintenance of good health for prolonged periods there are continuing complication with the method of administration, and the problem of poor utilization of intravenous nutrition, compared with oral nutrition, has yet to be solved. There is mounting evidence that the amino acid solutions that are available on the market do not provide the most efficient balance of "essential" and "non-essential" amino acids. Possibly the major problem in assessing the correct balance is establishing which amino acids are indispensable and determining the particular amino acid requirements of specific populations.

In a series of experiments in the 1940's and 1950's Rose et al., Nutr. Abstr. Rev. 27, 6731-647, defined a group of eight amino acids which were considered to be essential or indispensable for normal adult health. These amino acids—isoleucine, leucine, lysine, methionine, phenylalanine, threonine, tryptophan and valine—have since been shown in similar studies to be indispensable for women, children and infants (for a recent review see Laidlaw S. A. and Kopple, J. D. (1987) Am J. Clin Nutr 46, 593-605). It was tacitly assumed that the other amino acids were nonessential, and thus could be synthesized de novo from the eight essential amino acids.

In recent years with the improved techniques of amino acid analysis, and the development of chemically defined diets for parenteral and enteral nutrition the dispensibility of a number of classically considered nonessential amino acids has been questioned.

Tyrosine, for example, is considered to be a nonessential amino acid since under normal conditions it can be synthesized readily from phenylalanine via the phenylalanine hydroxylase reaction. This is the only pathway for de novo synthesis of tyrosine, and its inclusion in the diet exerts a sparing effect on the dietary phenylalanine requirement. Thus, when there is a deficiency in phenylalanine hydroxylase, as in classic phenylketonuria, an absolute requirement for tyrosine is expected.

There is now very good evidence to suggest that tyrosine is also indispensable for infants, and malnourished patients with alcoholic cirrhosis. Infants maintained on diets devoid of tyrosine showed decreased plasma tyrosine levels, impaired nitrogen retention and impaired weight gain, Snyderman S. E. (1971) *Metabolic Processes in the Fœtus and Newborn Infant* (Ionxix JHP, Visser HKA, Troelstra JD, eds.), pp. 128-141, Leiden: HE Stenfert Kroesse NV. The reintroduction of tyrosine to the infants diet normalized plasma tyrosine levels, and improved nitrogen retention and weight gain. Similarly, malnourished cirrhotic patients maintained on a standard parenteral nutrition solution (devoid of tyrosine) exhibited depressed tyrosine, cystine and taurine levels, markedly elevated phenylalanine and methionine levels, and remained in neutral or negative nitrogen balance, Rudman, D., Kutner, M. Ansley, J. et al. (1981) Gastroenterology 81, 1025-1035. When these patients were given an oral supplement containing tyrosine and cystine, nitrogen balance became strongly positive, plasma phenylalanine and methionine levels dropped, and plasma taurine, tyrosine and cystine levels rose to normal levels. It has been postulated that as for classic phenylketonuria infants and malnourished patients with cirrhosis have a hepatic deficiency in phenylalanine hydroxylase, Laidlaw SA and Kopple JD (1987) Am J Clin Nutr 46, 593-605.

Finally, there is suggestion that tyrosine may be required by patients undergoing intravenous nutrition therapy. It has been observed that in a group of non-stressed patients receiving 0.3 gN/kg/day of a commercially available intravenous solution, an amount well in excess of recommended daily requirements, that plasma levels of tyrosine, cysteine and glutamate remained in low fasting range while phenylalanine, leucine and isoleucine were increased to postprandial levels, Loder PB, Smith RC, Kee AJ, et al. (1990) Ann Surg (In Press). The rise in phenylalanine in relation to tyrosine may indicate inefficient conversion of phenylalanine to tyrosine in these non-stressed patients.

Based on this evidence there appears to be an absolute requirement for tyrosine (and cystine) in states of metabolic disorder, immaturity, or in severe stress. Furthermore, patients receiving intravenous nutrition may require more tyrosine and cystine than is available in current formulations.

Commercial intravenous nutrition solutions contain only a small amount of tyrosine & cysteine. This is because tyrosine and cysteine have limited solubility and the provision of even small amounts is difficult without the risk of precipitation. Additionally, some amino acids such as glutamine and asparagine are heat labile while others like cysteine, cystine and methionine are prone to oxidation.

A novel method of providing these otherwise difficult amino acids has been proposed through the use of dipeptides, Adibi SA (1987) Metabolism 36, 1001-1011. This suggestion has gained considerable attention as dipeptides have a number of additional advantages. Such advantages include (i) the ability to meet the nitrogen requirements of patients with severe fluid restriction such as the critically ill and renal failure patients and (ii) the reduction in hypertionicity of intravenous nutrition solutions by the substitution of amino acids with dipeptides permitting the possibility of intravenous nutrition delivery via a peripheral vein. Peripheral intravenous nutrition would avoid the hazards of central venous catheterization and reduce the complications of hypertonic solutions.

The initial investigations into the use of dipeptides as an amino acid and nitrogen source in intravenous nutrition commenced in the early 1970's. Since then extensive work performed on animal models have demonstrated the mechanisms of dipeptide clearance, the metabolism of the constituent amino acid residues, peptide utilization under conditions of constant infusion, peptide utilization under conditions of total parenteral nutrition, the influence of peptide structure on peptide metabolism, the potential of dipeptides as a sole nitrogen source in total parenteral nutrition, and the long term efficacy and safety of dipeptide mixtures, (Adibi SA (1987) Metabolism 36, 1001-1011 and Furst P, Albers S, Stehle P (1987) Contr Infusion Ther Clin Nutr 17, 117-136.

Clinical trials in man have just commenced and preliminary results support the conclusions drawn from animal models that dipeptides are a safe and efficacious alternative substrate for parenteral nutrition, Adibi SA (1989) Metabolism 38 (Suppl. 1), 89-92, Albers S. Wernerman, J. Stehle, P. et al. (1988) Clin. Sci. 75, 463-468, Alberts, S., Wernerman, J., Stehle, P., et al. (1989) Clin. Sci. 76, 643-648, Brandl M, Sailer, D., Langer, K., et al. (1987) Contr Infusion Ther. Clin. Nutr. 17, 103-116, Hubl, W., Druml, W., Langer, K., et al. (1989) Metabolism 38 (Suppl. 1), 59-62, Stehle, P., Zander, J., Mertes, N., et al. (1989) Lancet 1, 231-233 and Steininger, R., Karner, J., Roth, E., et al. (1989) Metabolism 38 (Suppl. 1), 78-81.

To date the peptides which have received most attention are glycl- and alanyl-dipeptides, Adibi SA (1987) Metabolism 36, 1001-1011, Adibi SA (1989) Metabolism 38 (suppl 1), 89-92, Furst, P., Albers, S., Stehle, P. (1987) Contr Infusion Ther Clin Nutr 17, 117-136. These dipeptides are thought by many, Adibi SA (1987) Metabolism 36, 1001-1011, to be more suitable for intravenous nutrition than other dipeptides with alternate N-terminal amino acid residues as they exhibit a more prolonged plasma half-life, and, thus a greater proportion of the infused dipeptides would reach the tissues intact. The rationale that dipeptides must reach the tissues intact for efficient utilization we believe to be unfounded. It is well know that intravenously administered free amino acid solutions are taken up and are utilized efficiently by the tissues of the body. In fact, this is the normal physiological situation; any peptides taken up by the intestinal mucosa and released into the portal blood stream are hydrolysed to their constituent amino acids before reaching the systemic circulation. Thus rapid hydrolysis of peptides in the blood stream should not hamper but should enhance utilization of amino acids by the tissues.

Furthermore, the infusion of peptide mixtures entirely based on glycyl- and alanyl-dipeptides may not be within the framework of physiological nutrition nor be applicable in clinical practice.

In this regard it must be remembered that glycine infused in excess is an inferior source of nitrogen, Jurgens, P., and Dolif, D. (1972) Parenteral nutrition (Wilkinson, ed.), pp. 77-92, Churchill Livingstone, London, and it is also questionable whether cells are able to cope with large intravenous loads of individual amino acids. Based on the problems associated with the above discussed peptides, an alternate method to deliver tyrosine and cystine than the n-terminal glycine or alanine carrier.

BRIEF SUMMARY OF THE INVENTION

This invention relates to a dipeptide, tyrosyl-arginine comprised of the amino acids tyrosine and arginine and the use of this dipeptide as a nutrient supplement to intravenous nutrition. Tyrosyle-arginine comprises from about three to ten grams per liter of an intravenous nutrition solution, and a median content of about five grams per liter of said solution. Other dipeptides tripeptides or free amino acids may be part of the intravenous nutrition solution. In addition, the intravenous nutrition solution may contain dextrose, lipid emulsions, vitamins, minerals and trace elements.

It is an object of this invention to provide an effective method to intravenously administer tyrosine using an important carrier, arginine, which may have beneficial effects. It is another object of this invention to provide increased tyrosine administration and concentrated nitrogen solutions for intensive care unit patients.

It is still another object of this invention to provide amino acid containing solutions that are less hypertonic than free amino acid solutions to allow peripheral intravenous nutrition.

It is yet still another object of the invention to use arginine to facilitate the removal of ammonia, to maintain immune function during sepsis and to enhance wound healing in trauma or burn patients.

BRIEF DESCRIPTION OF DRAWINGS

The present invention will be better understood from the description set forth below with reference to the accompanying drawings wherein:

FIG. 1 shows in vitro human Tyrosyl-arginine clearance.

DETAILED DESCRIPTION OF THE INVENTION

The system of lining "active" amino acids to a relatively "inactive," dispensable carrier amino acids, such as alanine and glycine, is not the most efficient or possible even the most effective way of administering amino acids in dipeptide form. A more efficient method is to link "active" or required amino acids. Tyrosine-Arginine (Tyr-Arg) is one such peptide which would allow the provision of tyrosine, which up to now has been difficult to administer because of its relative insolubility, with arginine an amino acid which has some specific and important nutritional and therapeutic attributes.

Arginine is regarded as non-essential for the maintenance of weight and nitrogen balance in adult mammals, Laidlaw, SA and Kopple, JD (1987) Am J Clin Nutr 46, 593-605. The endogenous pathways for arginine synthesis, outlined above, are apparently adequate in providing arginine in amounts required for weight and nitrogen balance maintenance. This is not the case, however, in many young growing mammalian species, i.e. rat, Scull, CW, Rose, WC (1930) J Biol Chem 89, 109-122, dog, Czarnecki, GL, Barker, DH (1984) J Nutr 114, 581-590, cat, Anderson PA, Baker, DH, Corgin JE (1979) J Nutr 109, 1368-1372, rabbits, Abel RM, Beck, CH, Abbott, WM, et al. (1973) N. Engl J. Med 288, 695-699 and pigs, Anderson LC, Lewis AJ, Peo ER, et al. (1984) J Amin Sci 58, 369-377, as exogenous arginine is required for maximal growth. Arginine has many properties which make it a suitable "active" carrier; it allows the formation of very water soluble peptides, it is very rapidly and efficiently metabolized, and there are secondary nutritional and metabolic benefits: Arginine is a key metabolite for many biochemical processes. Arginine plys a role in protein synthesis—as a substrate—, biosynthesis of other amino acids and associated derivatives, and is an important intermediate of the urea cycle. While arginine is essential for maximal growth in growing individuals, the other intermediates of the urea cycle, citrulline and ornithine, can substitute for arginine although the concentrations required to do so is greater than for arginine, Burns, RA, milner JA, Corbin JE (1981) J Nutr 111, 1020-1024.

There are many conditions where arginine is an essential nutrient. In most of these conditions the indispensability of arginine has arisen because of an abnormality in the urea cycle. Arginine facilitates the removal of ammonia, helps to maintain the immune system during sepsis, and can function to enhance healing in trauma or burn patients.

Parenteral infusions of essential amino acid solutions have been suggested as a treatment for patients with renal failure to reduce the severity of uremia while supplying essential nutrients, Abel, RM, Beck CH, Abbott WM, et al. (1973). Patients with urea cycle enzymnopathies require arginine as an indispensable nutrient irrespective of the specific enzymnopathy, Brusilow SW (1984) J Clin Invest 74, 2144-2148. Abnormal urea cycle function also occurs in Reye's Syndrome. This condition is characterized by a low hepatic activity of the mitochondrial enzymes carbamyl phosphate synthetase and ornithine transcarbamylase, Brown T, Hug G, Lansky L, et al. (1976) N Engl J Med 294, 861-867.

The body's ability to handle a large nitrogen load is dependent on a supply of arginine for effective removal of excess nitrogen. Infusions of large quantities of amino acids to both juvenile and adult animals and humans have been known to cause hyperammonemia and even coma unless the solutions contain either arginine, ornithine or citrulline, du Ruisseau JP, Greenstein JP, Winitz M, et al. (1956).

These results suggested an immediate clinical application, i.e., arginine as an agent to improve ammonia clearance by the liver in patients with liver disease. Although administration of arginine to such patients increases their total nitrogen load it appears to increase the liver's ability to remove ammonia in formation of urea, Fahey JL, Nathans D, Rairigh D (1957) Am J Med 23, 860-868. This has shown to decrease ammonia levels although studies of improvement of hepatic encephalopathy have not clearly demonstrated advantage in that respect, Fahey JL, Nathans D, Rairigh D (1957) Am J Med 23, 860-868. Further studies in a randomized and prospective fashion need to be undertaken to demonstrate the efficacy of arginine in the treatment of patients with encephalopathy.

There is also evidence that arginine increases the rate of collagen deposition following trauma. Experiments on dorsally wounded rats showed increased wound breaking strength and reparative collagen accumulation when the normal rat-chow was supplemented with arginine, Chyun JH, Griminger P (1984) J Nutr 114, 1697-1704 and Seifter E, Rettura G, Barbul A, et al. (1978) Surgery 84, 224-230.

Another aspect of the response to trauma in which arginine may play an important part is impaired host immunity. Central to this response is arginine's thymotropic action. Arginine increases thymic weight in uninjured rats and mice due to the increased leucocyte count within the thymus, Barbul A., Wasserkrug HL, Seifter E et al. (1980) Surg Res 29, 228-235. Associated with this is a stimulation of lymphocyte blastogenesis in response to mitogens, Barbul A, Wasserkrug, Seifter E, et al. (1980) J Surg Res 29, 228-235. Experiments in humans have also shown an effect of arginine on lymphocyte blastogenesis in response to a number of antigens, Barbul A (1986) J Parenter Enter Nutr 10, 227-238. This effect was seen in both healthy and injured humans, Barbul A (1986) J Parenter Enter Nutr 10, 227-238. While the beneficial effects of arginine as a carrier are thus evident and its choice forms part of the present invention, the clear advantages of tyrosyl-arginine as a vehicle to deliver tyrosine are exemplified in the following examples.

EXAMPLE 1

In vitro Clearance

Supplementation of an intravenous nutrition solution with the dipeptide tyrosyl-arginine facilitates the infusion of the poorly soluble amino acid tyrosine. We have initiated the first investigations into the metabolism of exogenous tyrosyl-arginine (TryArg). In vitro clearance of tyrosyl-arginine, and the constituent amino acids arginine and tyrosine was assessed in blood from two healthy normal volunteers on five occasions. Whole blood was incubated with tyrosyl-arginine (initially 547 nmol/ml) at 37°C. for 40 minutes. Throughout this period samples were taken to determine concentration of the dipeptide and individual amino acids. The following data was collected. The data is also plotted in FIG. 1.

TABLE 1

| | | \multicolumn{6}{c}{Time (min)} |
|---|---|---|---|---|---|---|---|
| | | 0 | 0.5 | 1.0 | 2.0 | 5.0 | 10.0 |
| Tyr—Arg | $\bar{x}$ | 547 | 389.85 | 338.65 | 278.94 | 245.52 | 220.90 |
| | s | — | 27.06 | 13.18 | 12.41 | 25.07 | 26.71 |
| Arg | $\bar{x}$ | 51.60 | 73.90 | 64.02 | 72.09 | 99.09 | 130.55 |
| | s | 7.31 | 12.51 | 10.31 | 1.87 | 10.35 | 25.64 |
| Tyr | $\bar{x}$ | 82.69 | 90.78 | 100.89 | 150.89 | 175.78 | 200.95 |
| | s | 7.69 | 5.58 | 10.89 | 12.68 | 15.32 | 18.73 |

| | | \multicolumn{4}{c}{Time (min)} |
|---|---|---|---|---|---|
| | | 20.0 | 40.0 | 60.0 | 120.0 |
| Tyr—Arg | $\bar{x}$ | 149.77 | 547.0 | 55.57 | 0 |
| | s | 41.45 | 13.04 | 5.69 | 0 |
| Arg | $\bar{x}$ | 284.34 | 207.38 | 149.91 | 65.39 |
| | s | 15.89 | 10.98 | 8.65 | 5.69 |
| Tyr | $\bar{x}$ | 250.35 | 270.68 | 250.98 | 100.59 |
| | s | 26.68 | 20.87 | 25.89 | 12.83 |

Tyrosyl-arginine concentration in human whole blood fell biexponentially with a half-time of 4.2 minutes; degradation was complete by 2 hours. There was a concomitant rise in arginine and tyrosine concentration in human blood which subsequently fell gradually to baseline over 2 hours.

EXAMPLE 2

In Vivo Clearance

In vivo clearance was assessed in five large (370 g) mature (122 days old) Sprague Dawley rats. The animals were anaesthetised with sodium pentabarbitone and remained anaesthetised during the entire procedure. A large bolus of tyrosyl-arginine (82.1 2.8 µg/g rat, Mean SD) was injected intravenously into a central vein and rapid blood samples (n=11) (total volume=2.0 ml) were obtained through a central venous catheter over 20 minutes. We observed that tyrosyl-arginine was cleared rapidly by rats with an approximate half life of 30 seconds. There was a large and rapid rise in Arg concentration reaching a maximum after 2.5 min and falling to baseline levels after 20 minutes.

Method of Administration

The aqueous dipeptide tyrosyl-arginine, or other dipeptides, or indeed oligopeptides may be ingested orally along with other nutrients such as conventional foods or prepared vitamins, fats, glucose, oligosaccharides, minerals and trace elements. For parenteral administration, a supply of the oligopeptide solution may be merged through a Y-connection with a supply of glucose solution or other parenteral solutions. The peptide solutions may be mixed with glucose solutions and/or other parenteral solutions to create a mixture which may be administered parenterally.

The administration of peptides rather than free amino acids allows administration of the same amount of amino acid residue in solutions which are less hypertonic and therefore can be introduced into peripheral veins, which is not considered to be a surgical procedure.

Although the invention has been shown in connection with certain specific embodiments, it will be readily apparent to those skilled in the art that various changes in form and arrangement of steps can be made to suit requirements without departing from the spirit and scope of the invention.

We claim:

1. A nutrient composition comprising free amino acids, and tyrosyl-arginine.

2. The composition of claim 1 wherein tyrosyl-arginine comprises from between three to ten grams per liter of said solution.

3. The nutrient composition of claim 1 including other nutrient selected from the class consisting of lipid emulsions, glucose, oligosaccharides, minerals, trace elements, vitamins and oligopeptides.

4. A peripheral intravenous nutritional solution comprising free amino acids and a dipeptide tyrosyl-arginine.

5. The solution of claim 4 wherein said dipeptide comprises from between three to ten grams per liter of said solution.

6. A method to provide intravenously administered nutrition to a patient in states of metabolic disorder, immaturity or severe stress comprising adding a dipeptide tyrosyl-arginine to an intravenous nutritional formulation.

7. The method of claim 6 wherein said dipeptide comprises from between three to ten grams per liter of said solution.

8. The method of claim 6 wherein said intravenous nutritional formulation is administered peripherally.

* * * * *